United States Patent [19]

Falling et al.

[11] Patent Number: 5,254,701
[45] Date of Patent: Oct. 19, 1993

[54] PROCESS FOR THE PRODUCTION OF MIXTURES OF 2-HYDROXYTETRAHYDROFURAN AND 4-HYDROXYBUTANAL

[75] Inventors: Stephen N. Falling, Kingsport, Tenn.; Gerald W. Phillips, Longview, Tex.

[73] Assignee: Eastman Kodak Company, Rochester, N.Y.

[21] Appl. No.: 702,483

[22] Filed: May 20, 1991

[51] Int. Cl.$^5$ .................... C07D 307/20; C07C 45/59
[52] U.S. Cl. .................... 549/475; 568/483
[58] Field of Search ................ 549/475; 568/483

[56] References Cited

U.S. PATENT DOCUMENTS

| | | | |
|---|---|---|---|
| 2,556,325 | 6/1951 | Fluchaire et al. | 549/507 |
| 4,529,808 | 7/1985 | Lin et al. | 549/475 |
| 4,533,742 | 8/1985 | Lin et al. | 549/475 |
| 4,539,415 | 9/1985 | Mueller et al. | 549/475 |
| 5,008,408 | 4/1991 | Fischer et al. | 549/475 |

FOREIGN PATENT DOCUMENTS 1248669  8/1967  Fed. Rep. of Germany .

OTHER PUBLICATIONS

*Chemical Abstracts,* 46:3995f (Mar. 1949).
R. Paul et al., *Bull. Soc. Chim. France,* pp. 668–671 (1950).
L. Lombardo et al., *Aust. J. Chim.,* 27, pp. 143–152 (1974).
*Chemical Abstracts,* 91:175179w (1979).
*Chemical Abstracts,* 91:20308p (Mar. 1979).
A. Polo et al., *J. Chem. Soc., Chem. Commun.,* pp. 600–601 (1990).
K. Hirai et al., *Chemical Letters,* pp. 23–26 (1982).
*Chemical Abstracts,* 43:3816, *Comp. Rend.,* 228, 102–104 (1949).
H. A. Bates et al., *J. Org. Chem.,* 50, pp. 3843–3845 (1985).
N. A. Bergman et al., *J. Org. Chem.,* 52, pp. 4449–4450 (1987).
C. D. Hurd et al., *J. Am. Chem. Soc.,* 74, pp. 5324–5326 (1952).

*Primary Examiner*—C. Warren Ivy
*Assistant Examiner*—A. Owens
*Attorney, Agent, or Firm*—J. Frederick Thomsen; William P. Heath, Jr.

[57] ABSTRACT

Disclosed is a process for the production of an equilibrium mixture of 2-hydroxytetrahydrofuran and 4-hydroxybutanal by a two-step process comprising (1) heating 2,5-dihydrofuran in the presence of a catalyst system comprising a phosphine, ruthenium or rhodium to convert the 2,5-dihydrofuran to 2,3-dihydrofuran; and (2) contacting 2,3-dihydrofuran with water in the presence of an acidic catalyst to convert the 2,3-dihydrofuran to a mixture of 2-hydroxytetrahydrofuran and 4-hydroxybutanal. Also disclosed is a process for the continuous production of an aqueous solution of 2-hydroxytetrahydrofuran and 4-hydroxybutanal. The mixture of 2-hydroxytetra-hydrofuran and 4-hydroxybutanal may be catalytically hydrogenated to produce 1,4-butanediol.

13 Claims, No Drawings

PROCESS FOR THE PRODUCTION OF MIXTURES OF 2-HYDROXYTETRAHYDROFURAN AND 4-HYDROXYBUTANAL

This invention pertains to a process for the preparation of mixtures of 2 hydroxytetrahydrofuran and 4 hydroxybutanal. More specifically, this invention pertains to a two-step process for converting 2,5-dihydrofuran to a mixture of 2-hydroxytetra-hydrofuran and 4 hydroxybutanal which may be hydrogenated to 1,4-butanediol, a valuable polymer intermediate.

Commercial processes used to make 1,4-butanediol include a two-step Reppe process wherein acetylene is reacted with formaldehyde to produce 2-butyn-1,4-diol which is then hydrogenated to 1,4-butanediol. In a more recent process, propylene oxide is converted to 1-propen-3-ol which is hydroformylated in the presence of a rhodium catalyst to produce a mixture of 2-hydroxytetrahydrofuran and 4-hydroxybutanal which is hydrogenated to 1,4-butanediol. Most 1,4-butanediol produced is used in the manufacture of polymers, including polyurethanes and poly(tetramethylene terephthalate) and in the production of tetrahydrofuran.

Processes are known for the preparation of 2,5-dihydrofuran from butadiene. U.S. Pat. Nos. 4,897,498 and 4,950,773 describe the preparation of 3,4-epoxy-1-butene by the selective monoepoxidation of butadiene. Processes for the isomerization or rearrangement of 3,4-epoxy-1-butene to 2,5-dihydrofuran are described in U.S. Pat. Nos. 3,932,468 and 3,996,248. Processes have been developed for the isomerization of 3,4-epoxy-1-butene to 2,5-dihydrofuran wherein an organic, quaternary onium iodide compound, optionally in combination with certain organometallic compounds such as organotin iodides, is employed to catalyze the isomerization process.

The process of the present invention provides a means for the production of an equilibrium mixture of 2-hydroxytetrahydrofuran and 4-hydroxybutanal by the steps of:

(1) heating 2,5-dihydrofuran in the presence of a catalyst system comprising a tertiary phosphine and ruthenium or rhodium to convert the 2,5-dihydrofuran to 2,3-dihydrofuran; and (2) contacting 2,3-dihydrofuran with water in the presence of an acidic catalyst to convert the 2,3-dihydrofuran to a mixture of 2-hydroxytetrahydrofuran and 4-hydroxybutanal.

In an optional third step, the aqueous solution derived from step (2) is catalytically hydrogenated to produce an aqueous solution of 1,4-butanediol.

In the first step of the process, 2,5-dihydrofuran is heated at a temperature of about 20° C. to 100° C., preferably 50° C. to 70° C., in the presence of a catalytically-effective amount of a catalyst system comprising a tertiary phosphine and rhodium or, preferably, ruthenium to isomerize the 2,5-dihydrofuran to 2,3-dihydrofuran. The tertiary phosphine, rhodium, and ruthenium compounds which may be used as components of the catalyst system are known compounds and/or can be prepared according to known procedures. The catalytically active species of the catalyst system comprise rhodium (I) or ruthenium (I) in complex association with at least 1 tertiary phosphine molecule per atom of rhodium or ruthenium. In addition to the phosphine ligands, other ligands which may be present in the catalyst complexes include carbon monoxide, hydrogen, carbonyl compounds such as diketones and halogen such as chloro, bromo and iodo.

The components of the catalyst system may be provided either as a preformed complex of rhodium or ruthenium or as separate components. Examples of the preformed complexes are represented by rhodium and ruthenium complexes having general formulas (I) and (II):

$$RhH_m[CO]_nX_pY_q \quad \text{(I)}$$

$$RuH_m[CO]_nX_pY_q \quad \text{(II)}$$

wherein X is a halogen atom such as chloro, bromo or iodo, Y is a tertiary (trisubstituted) phosphine molecule, m is 0 to 3, n is 0 to 5, p is 0 to 4, and q is 1 to 4 and the sum of m+n+p+q is 4 to 6. Examples of the phosphine ligands which Y may represent include tributylphosphine, butyldiphenyl-phosphine, tribenzylphosphine, tricyclohexylphosphine, 1,2-bis(diphenylphosphino)ethane, 1,3-bis(diphenylphosphino) propane, 2,2'-bis(diphenylphosphinomethyl)-1,1'-biphenyl, and 1,2-bis(diphenylphosphinomethyl)benzene. Additional examples of tertiary phosphines are disclosed in U.S. Pat. Nos. 4,845,306, 4,742,178, 4,774,362, 4,871,878 and 4,960,949. Typical phosphine ligands may be represented by the general formula

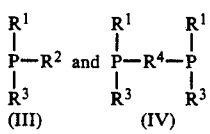

$$\begin{array}{ccc} R^1 & & R^1 \quad R^1 \\ | & & | \quad\quad | \\ P{-}R^2 & \text{and} & P{-}R^4{-}P \\ | & & | \quad\quad | \\ R^3 & & R^3 \quad R^3 \\ \text{(III)} & & \text{(IV)} \end{array}$$

wherein $R^1$, $R^2$ and $R^3$ are the same or different and each is hydrocarbyl containing up to about 12 carbon atoms and $R^4$ is a hydrocarbylene group which links the 2 phosphorus atoms through a chain of 2 to 8 carbon atoms. Examples of the hydrocarbyl groups which $R^1$, $R^2$ and $R^3$ may represent include alkyl including aryl-substituted alkyl such as benzyl, cycloalkyl such as cyclohexyl, and aryl such as phenyl and phenyl substituted with one or more alkyl groups. Alkylene such as ethylene, trimethylene and hexamethylene, cycloalkylene such as cyclohexylene, and phenylene, naphthlene and biphenylene are examples of the hydrocarbylene groups which $R^4$ may represent. The following are specific examples of suitable preformed catalytic systems: dihydridotetrakis-(triphenylphosphine)ruthenium ($RuH_2(Ph_3P)_4$), carbonyl-chlorohydridotris(triphenylphosphine)ruthenium $RuClH(CO)(Ph_3P)_3$, chlorohydridotris(triphenylphosphine)ruthenium ($RuHCl(Ph_3P)_3$), dichlorotris(triphenylphosphine)ruthenium ($RuCl_2(Ph_3P)_3$), chlorotris(triphenylphosphine)rhodium ($RhCl(Ph_3P)_3$), and hydridocarbonyltris-(triphenylphosphine)rhodium ($RhH(CO)(Ph_3P)_3$).

The tertiary phosphine, rhodium and ruthenium components of the catalyst system may be provided to the isomerization process as separate compounds provided that at least 1 mole of tertiary phosphine is used per gram-atom of rhodium or ruthenium. Examples of tertiary phosphine compounds which may be used are set forth hereinabove. The form in which the rhodium and ruthenium catalyst components are provided is, in general, not critical to the operation of the isomerization process. For example, the rhodium and ruthenium may be supplied in the form of their halides, carbonyl halides or carbonylacetylacetonates. The amount of phosphine compound used should be at least one mole phosphine compound per gram atom of rhodium or ruthenium. Larger amounts of tertiary phosphine compound, amounts which give a mole phosphine:gram-atom Rh or Ru of up to 10, may be used and may be advantageous depending on the particular form in which the rhodium or ruthenium is provided to the catalyst system.

The catalytically effective amount of the catalyst system is in the range of about 0.001 to 10 millimoles (mmole) of rhodium or ruthenium complex per mole of 2,5-dihydrofuran, preferably about 0.01 to 0.1 mmoles of catalyst complex per mole of 2,5-dihydrofuran. The pressure at which the first step is carried out is not important and thus pressures moderately above or below atmospheric pressures may be used although the isomerization step preferably is conducted at approximately ambient pressure.

The first step of the process optionally may be carried out in the presence of an inert solvent, i.e., a solvent in which the 2,5-dihydrofuran, the catalyst and the 2,3-dihydrofuran are soluble. Examples of such solvents include aliphatic, cycloaliphatic and aromatic hydrocarbons such as toluene, benzene, xylene, heptane and cyclohexane; ethers such as tetrahydrofuran; alkanols such as methanol and ethanol; and esters of alkanols and aliphatic carboxylic acids such as ethyl acetate. It is preferred, however, that an extraneous solvent not be used.

The first step of the process of the present invention may be carried out either as a batch or continuous operation. A particularly advantageous mode of operation comprises the steps of (i) continuously feeding 2,5-dihydrofuran to an isomerization zone containing 2,5-dihydrofuran, 2,3-dihydrofuran and a catalytic amount of a phosphine complex of rhodium or ruthenium and (ii) continuously removing 2,3-dihydrofuran as a vapor from the isomerization zone. When operating at ambient pressure, the temperature of the isomerization zone necessarily will be maintained at about 55° to 65° C. since the boiling points of 2,3-dihydrofuran and 2,5-dihydrofuran are 55° and 66° C., respectively.

The second step of our novel process may be carried out by contacting, at a temperature in the range of about 10° to 100° C., normally at a temperature in the range of about 20° to 70° C., 2,3-dihydrofuran, water and an acidic catalyst. The amount of water typically used gives a water:2,3-dihydrofuran weight ratio in the range of about 1:1 to 10:1. Acids which can be used for this step are inorganic acids such as hydrochloric acid, sulfuric acid, and phosphoric acid and organic acids such as carboxylic acids, e.g., acetic acid and propionic acid, and sulfonic acids, e.g., methanesulfonic acid, benzenesulfonic acid, and mixed or specific isomers of p-toluenesulfonic acid. Acidic, ion exchange resins are particularly useful for this reaction since they are insoluble in the reaction mixture and thereby simplify the separation of the acidic catalyst from the aqueous 2-hydroxytetrahydrofuran/4-hydroxybutanal mixture by filtration. Examples of such insoluble polymeric acids include sulfonated polystyrene resins, e.g., Amberlyst 15 beads, and sulfonated polyfluorocarbon resins, e.g., Nafion-H resin. The catalytically effective amount of the acidic catalyst can vary substantially depending on the particular acidic material used and the mode of operation. For example, when using a strong, homogeneous acid such as sulfuric acid or a sulfonic acid such as toluenesulfonic acid, sufficient acid is used to give to the aqueous phase of the reaction mixture a pH of less than about 6.5, preferably about 1.0 to 5.0.

The second step of the process may be operated batchwise or continuously. For example, in continuous operation, 2,3-dihydrofuran and water may be continuously fed, either separately or as a mixture, to a hydrolysis zone comprising a vessel packed with or containing one or more beds of an acidic, ion exchange resin wherein the feed mixture intimately contacts the acidic catalyst. An aqueous solution of an equilibrium mixture of 2-hydroxytetrahydrofuran and 4-hydroxybutanal isomers is continuously removed from the hydrolysis zone. The effluent from the hydrolysis zone normally contains minor amounts, e.g., up to 20 weight percent based on the weight of the organic materials, of the acetals bis(tetrahydro-2-furanyl)ether (two diastereomers) and 4-(tetrahydro-2-furanyloxy)butanal.

The aqueous product obtained from the second step of the process may be hydrogenated directly to an aqueous solution of 1,4-butanediol by contacting the aqueous product with hydrogen in the presence of a hydrogenation catalyst such as a Group VIII metal, e.g., nickel, ruthenium, platinum, palladium, and the like. The catalytic metal may be supported on an inert support such as silica, alumina, carbon, titania, molecular sieves, zeolites, Kieselguhr, and silica-alumina. Raney nickel is the preferred catalyst. The hydrogenation process may be operated batchwise or continuously using hydrogenation-effective conditions of temperature, pressure and contact time. For example, the hydrogenation can be carried out over a temperature range of about 25° to 200° C., preferably 50° to 100° C., and a pressure in the range of about 1 to 345 bar absolute (approximately 15 to 5000 pounds per square inch absolute), preferably about 52 to 104 bar absolute (approximately 750 to 1500 psia). Continuous hydrogenation may be carried out by feeding the effluent from the hydrolysis zone to a vertical hydrogenation reaction vessel provided with an internal ejection device to promote agitation of the reaction medium with a flow of excess hydrogen gas. The exothermic reaction occurs adiabatically at about 50° C. to 75° C. and 100 bar absolute in the presence of finely divided Raney nickel suspended in the reaction mixture Aqueous 1,4-butane-diol containing a small amount of entrained catalyst is removed continuously from the upper section of hydrogenation reactor and filtered to remove the catalyst. The water present in the hydrogenation product may be removed by distillation under reduced pressure. For example, the hydrogenation product may be fed to the side of a distillation column operated at a base temperature in the range of about 125° C.to 175° C. and a base pressure of about 100 to 150 torr. Water is distilled overhead and 1,4-butanediol having a purity greater than 95% is removed from the base of the column. Alternatively, the water may be removed from the 1,4-butanediol by azeotropic distillation using a water immiscible entrainer such as toluene.

In a preferred embodiment, the present invention provides a process for the continuous production of an aqueous solution of 2-hydroxytetrahydrofuran and 4-hydroxybutanal by the steps of:

(i) continuously feeding 2,5-dihydrofuran to an isomerization zone containing 2,5-dihydrofuran, 2,3-dihydrofuran and a catalytic amount of a catalyst system comprising a tertiary phosphine and rhodium or ruthenium;

(ii) continuously removing 2,3-dihydrofuran as a vapor from the isomerization zone;

(iii) continuously feeding 2,3-dihydrofuran and water to a hydrolysis zone comprising a vessel packed with or containing one or more beds of an acidic, ion exchange resin wherein the 2,3-dihydrofuran and water intimately contact the acidic catalyst; and (iv) continuously removing an aqueous solution of 2-hydroxytetrahydrofuran and 4-hydroxybutanal from the hydrolysis zone.

The process provided by the present invention is further illustrated by the following examples. Gas chromatographic (GC) analyses were performed on a Hewlett Packard 5890A gas chromatograph with a DB5-30W capillary column; temperature program 35° C. (4.5 minutes), 20° C./minute to 260° C. (hold 6 minutes).

EXAMPLE 1

A flask was charged with 86.8 mg (0.0911 mmole) of carbonylchlorohydridotris(triphenylphosphine)ruthenium (RuClH(CO)(Ph$_3$P)$_3$) and 46.73 g (0.667 mole) of freshly distilled 2,5-dihydrofuran. The mixture was brought to reflux under a nitrogen atmosphere. During reaction the pot temperature gradually dropped from 65° C. to 55° C. After 2.5 hours the reaction was complete as determined by GC analysis. The mixture was distilled to give 44.91 g of product at 53–55° C. (96.1% yield). By GC analysis, the product consisted of 98.5% 2,3-dihydrofuran, 0.47% 2,5-dihydrofuran, and 1.14% tetrahydrofuran (the starting material contained 1.33% tetrahydrofuran).

EXAMPLE 2

A flask was charged with 88.6 mg (0.0924 mmole) of dichlorotris(triphenylphosphine)ruthenium (RuCl$_2$(Ph$_3$P)$_3$) and 48.65 g (0.694 mole) of 2,5-dihydrofuran. After 47 hours at reflux the mixture was distilled to give 45.76 g of product at 53–54° C. (94.1% yield). The product consisted of 98.7% 2,3-dihydrofuran, 0.33% 2,5-dihydrofuran, and 1.02% tetrahydrofuran.

EXAMPLE 3

A flask was charged with 73.4 mg (0.0794 mmole) of chlorohydridotris(triphenylphosphine)ruthenium (RuHCl(Ph$_3$P)$_3$) and 46.05 g (0.657 mole) of 2,5-dihydrofuran. After 21 hours at reflux the mixture was distilled to give 43.15 g of product at 53–54° C. (93.7% yield). The product consisted of 98.4% 2,3-dihydrofuran, 0.33% 2,5-dihydrofuran, and 1.12% tetrahydrofuran.

EXAMPLE 4

A flask was charged with 1077 mg (0.0935 mmole) of dihydridotetrakis(triphenylphosphine)ruthenium (RuH$_2$(Ph$_3$P)$_4$) and 49.83 g (0.711 mole) of 2,5-dihydrofuran. After 34 hours at reflux the mixture was distilled to give 47.44 g of product at 53–54° C. (95.2% yield). The product consisted of 96.3% 2,3-dihydrofuran, 2.69% 2,5-dihydrofuran, and 0.99% tetrahydrofuran.

EXAMPLE 5

A flask was charged with 86.3 mg (0.0939 mmole) of hydridocarbonyltris(triphenylphosphine)rhodium (RhH(CO)(Ph$_3$P)$_3$) and 52.95 g (0.755 mole) of 2,5-dihydrofuran. After 90 minutes at reflux the mixture was distilled to give 51.02 g of product at 51–55° C. (96.4% yield). The product was 97.6% 2,3-dihydrofuran, 0.8% furan, 0.29% 2,5-dihydrofuran and 1.29% tetrahydrofuran.

EXAMPLE 6

To a 1000 mL, three neck, flask equipped with a 15-plate Oldershaw column, addition funnel, thermometer, and magnetically-controlled distillation head was charged 0.35 g (0.37 mmole) of carbonylchlorohydridotris(triphenylphosphine)ruthenium (RuClH(CO)(Ph$_3$P)$_3$) and 200 g of 2,5-dihydrofuran. To the addition funnel was charged 181.6 g (5.44 moles total) of 2,5-dihydrofuran. The mixture was refluxed for two hours then distillate was collected at a reflux:take-off ratio of 4 to 1 and a head temperature of 52.9–53.4° C. As distillate was collected, new 2,5-dihydrofuran was added to the pot at a similar rate over four hours. The distillation was then continued to a head temperature of 54.1° C. A total of 313.3 g of distillate (82.1% yield) consisting of 98.1% 2,3-dihydrofuran, 1.52% 2,5-dihydrofuran, and 0.39% tetrahydrofuran was obtained.

EXAMPLE 7

To a flask was charged 70.45 g (1.005 mole) of 2,3-dihydrofuran, 250 mL of water and 5.02 g of water-washed (Soxhlet) Amberlyst 15 acidic, ion exchange resin (Rohm and Haas). The two layer mixture was rapidly stirred for 30 minutes to effect hydrolysis. During hydrolysis the temperature rose to 52° C. over 15 minutes and the mixture became homogeneous. GC analysis showed 86.4% 2-hydroxytetrahydrofuran/4-hydroxybutanal, 3.73% bis(tetrahydro-2-furanyl)ether diastereomers, and 9.91% 4-tetrahydro-2-furanyl)butanal. The mixture was vacuum filtered and rinsed with 75 mL of water. The clear solution was hydrogenated at 59–61° C. and 103 bars absolute (approximately 1500 psig) for five hours over 10 g of Raney nickel. GC analysis showed that the resulting solution contained 1,4-butanediol and no starting materials. After filtering off the catalyst, water was removed from the clear, colorless solution at a bath temperature of about 50° C. and a pressure of about 30 torr by means of a rotary evaporator. The light yellow, crude 1,4-butanediol (93.15 g) was vacuum distilled at 8.8 torr to give a product fraction (81.53 g, 90.0% yield) boiling at 113–119° C. The product assay was 96.6% 1,4-butanediol and 1.52% butyrolactone.

The invention has been described in detail with particular reference to preferred embodiments thereof, but it will be understood that variations and modifications can be effected within the spirit and scope of the invention.

I claim:

1. Process for the production of a mixture of 2-hydroxytetrahydrofuran and 4-hydroxybutanal by the steps of:

(1) heating 2,5-dihydrofuran in the presence of a catalyst system comprising a tertiary phosphine and ruthenium or rhodium to convert the 2,5-dihydrofuran to 2,3-dihydrofuran; and (2) contacting 2,3-dihydrofuran with water in the presence of an acidic catalyst to convert the 2,3-dihydrofuran to a mixture of 2-hydroxytetrahydrofuran and 4-hydroxybutanal.

2. Process according to claim 1 for the production of a mixture of 2-hydroxytetrahydrofuran and 4-hydroxybutanal by the steps of:
(1) heating 2,5-dihydrofuran at a temperature of about 20° C. to 100° C. in the presence of a catalytic amount of a catalyst system comprising a tertiary phosphine and ruthenium or rhodium wherein the ratio of moles phosphine:gram atoms ruthenium or rhodium is a least 1:1 to convert the 2,5-dihydrofuran to 2,3-dihydrofuran; and
(2) contacting 2,3-dihydrofuran with water at a temperature of 10° C. to 100° C. in the presence of an acidic catalyst to convert the 2,3-dihydrofuran to a mixture of 2-hydroxytetrahydrofuran and 4-hydroxybutanal.

3. Process according to claim 2 wherein the step (1) catalyst system comprises a phosphine ruthenium complex having the formula $RuH_m[CO]_nX_pY_q$ wherein X is a halogen atom such as chloro, bromo or iodo, Y is a tertiary phosphine molecule, m is 0 to 3, n is 0 to 5, p is 0 to 4, and q is 1 to 4 and the sum of m+n+p+q is 4 to 6.

4. Process according to claim 2 wherein the step (1) catalyst system comprises a phosphine rhodium complex having the formula $RhH_m[CO]_nX_pY_q$ wherein X is a halogen atom such as chloro, bromo or iodo, Y is a tertiary phosphine molecule, m is 0 to 3, n is 0 to 5, p is 0 to 4, and q is 1 to 4 and the sum of m+n+p+q is 4 to 6.

5. Process for the production of a mixture of 2-hydroxytetrahydrofuran and 4-hydroxybutanal by the steps of:
(1) heating 2,5-dihydrofuran at a temperature of about 50° C. to 70° C. in the presence of a catalytic amount of a catalyst system comprising a tertiary phosphine and ruthenium or rhodium wherein the ratio of moles phosphine:gram atoms ruthenium or rhodium is a least 1:1 to convert the 2,5-dihydrofuran to 2,3-dihydrofuran; and
(2) contacting 2,3-dihydrofuran with water at a temperature of 20° to 70° C. in the presence of an acidic, ion exchange resin to convert the 2,3-dihydrofuran to a mixture of 2-hydroxytetrahydrofuran and 4-hydroxybutanal.

6. Process according to claim 5 wherein the catalyst system comprises a phosphine ruthenium complex having the formula $RuH_m[CO]_nX_pY_q$ wherein X is a halogen atom such as chloro, bromo or iodo, Y is a tertiary phosphine molecule, m is 0 to 3, n is 0 to 5, p is 0 to 4, and q is 1 to 4 and the sum of m+n+p+q is 4 to 6.

7. Process according to claim 5 wherein the catalyst system comprises a phosphine-rhodium complex having the formula $RhH_m[CO]_nX_pY_q$ wherein X is a halogen atom such as chloro, bromo or iodo, Y is a tertiary phosphine molecule, m is 0 to 3, n is 0 to 5, p is 0 to 4, and q is 1 to 4 and the sum of m+n+p+q is 4 to 6.

8. Process for the continuous production of an aqueous solution of 2 hydroxytetrahydrofuran and 4-hydroxybutanal by the steps of:
(i) continuously feeding 2,5-dihydrofuran to an isomerization zone containing 2,5-dihydrofuran, 2,3-dihydrofuran and a catalyst system comprising a tertiary phosphine and ruthenium or rhodium wherein the ratio of moles phosphine:gram-atoms ruthenium or rhodium is a least 1:1;
(ii) continuously removing 2,3-dihydrofuran as a vapor from the isomerization zone;
(iii) continuously feeding 2,3-dihydrofuran and water to a hydrolysis zone comprising a vessel packed with or containing one or more beds of an acidic, ion exchange resin wherein the 2,3-dihydrofuran and water intimately contact the acidic catalyst; and
(iv) continuously removing an aqueous solution of 2-hydroxytetrahydrofuran and 4-hydroxybutanal from the hydrolysis zone.

9. Process according to claim 8 for the continuous production of an aqueous solution of 2-hydroxytetrahydrofuran and 4-hydroxybutanal by the steps of:
(i) continuously feeding 2,5-dihydrofuran to an isomerization zone maintained at about 55° C. to 65° C. and containing 2,5-dihydrofuran, 2,3-dihydrofuran and a catalytic amount of a catalyst system comprising a tertiary phosphine and ruthenium or rhodium wherein the ratio of moles phosphine:gramatoms ruthenium or rhodium is a least 1:1;
(ii) continuously removing 2,3-dihydrofuran as a vapor from the isomerization zone;
(iii) continuously feeding 2,3-dihydrofuran and water to a hydrolysis zone comprising a vessel packed with or containing one or more beds of an acidic, ion exchange resin wherein the 2,3-dihydrofuran and water intimately contact the acidic catalyst at about 20° to 70° C.; and
(iv) continuously removing an aqueous solution of 2-hydroxytetrahydrofuran and 4-hydroxybutanal from the hydrolysis zone.

10. Process according to claim 9 wherein the step (1) catalyst system comprises a phosphine-ruthenium complex having the formula $RuH_m[CO]_nX_pY_q$ wherein X is a halogen atom such as chloro, bromo or iodo, Y is a tertiary phosphine molecule, m is 0 to 3, n is 0 to 5, p is 0 to 4, and q is 1 to 4 and the sum of m +n+p+q is 4 to 6.

11. Process according to claim 9 wherein the step (1) catalyst system comprises a phosphine-rhodium complex having the formula $RhH_m[CO]_nX_pY_q$ wherein X is a halogen atom such as chloro, bromo or iodo, Y is a tertiary phosphine molecule, m is 0 to 3, n is 0 to 5, p is 0 to 4, and q is 1 to 4 and the sum of m +n+p+q is 4 to 6.

12. Process for the production of a mixture of 2-hydroxytetrahydrofuran and 4-hydroxybutanal by the steps of:
(1) heating 2,5-dihydrofuran in the presence of a catalyst system comprising a tertiary phosphine and ruthenium or rhodium to convert the 2,5-dihydrofuran to 2,3-dihydrofuran; and
(2) contacting 2,3-dihydrofuran with water in the presence of an acidic catalyst selected from inorganic acids, organic acids and acidic, ion exchange resins to convert the 2,3-dihydrofuran to a mixture of 2-hydroxytetrahydrofuran and 4-hydroxybutanal.

13. Process according to claim 12 for the production of a mixture of 2-hydroxytetrahydrofuran and 4-hydroxybutanal by the steps of:
  (1) heating 2,5-dihydrofuran at a temperature of about 20° C. to 100° C. in the presence of a catalytic amount of a catalyst system comprising a tertiary phosphine and ruthenium or rhodium wherein the ratio of moles phosphine:gram-atoms ruthenium or rhodium is a least 1:1 to convert the 2,5-dihydrofuran to 2,3-dihydrofuran; and
  (2) contacting 2,3-dihydrofuran with water at a temperature of 10° C. to 100° C. in the presence of an acidic catalyst selected from inorganic acids, organic acids and acidic, ion exchange resins to convert the 2,3-dihydrofuran to a mixture of 2-hydroxytetrahydrofuran and 4-hydroxybutanal.

* * * * *